(12) United States Patent
Bertaux

(10) Patent No.: US 9,851,299 B2
(45) Date of Patent: Dec. 26, 2017

(54) METHOD OF ANALYZING AIR QUALITY

(71) Applicant: Isle Management Co., Vero Beach, FL (US)

(72) Inventor: Gregory Bertaux, Vero Beach, FL (US)

( * ) Notice: Subject to any disclaimer, the term of this patent is extended or adjusted under 35 U.S.C. 154(b) by 34 days.

(21) Appl. No.: 14/887,819

(22) Filed: Oct. 20, 2015

(65) Prior Publication Data

US 2016/0116405 A1   Apr. 28, 2016

Related U.S. Application Data

(60) Provisional application No. 62/068,643, filed on Oct. 25, 2014.

(51) Int. Cl.
| | |
|---|---|
| *G01N 21/49* | (2006.01) |
| *G01N 33/00* | (2006.01) |
| *G01N 1/22* | (2006.01) |
| *G01N 15/02* | (2006.01) |
| *G01N 15/06* | (2006.01) |
| G01N 15/00 | (2006.01) |
| G01N 35/00 | (2006.01) |
| G01N 15/10 | (2006.01) |
| G01N 15/14 | (2006.01) |

(52) U.S. Cl.
CPC .......... *G01N 21/49* (2013.01); *G01N 1/2273* (2013.01); *G01N 15/0227* (2013.01); *G01N 15/0612* (2013.01); *G01N 15/0637* (2013.01); *G01N 15/1463* (2013.01); *G01N 33/0011* (2013.01); G01N 35/00009 (2013.01); G01N 2015/0046 (2013.01); G01N 2015/0065 (2013.01); G01N 2015/1006 (2013.01); G01N 2015/1486 (2013.01); G01N 2015/1493 (2013.01)

(58) Field of Classification Search
CPC ............... G01N 21/49; G01N 33/0011; G01N 15/0227; G01N 15/0612; G01N 15/0637; G01N 2015/0065; G01N 2015/0046; G01N 2015/1493; G01N 21/64
See application file for complete search history.

(56) References Cited

U.S. PATENT DOCUMENTS

| | | | | |
|---|---|---|---|---|
| 4,140,912 | A * | 2/1979 | Bressan | .............. G01T 7/04 250/394 |
| 6,122,053 | A | 9/2000 | Zwaal | |
| 6,960,756 | B1 | 11/2005 | Penumadu | |
| 7,302,313 | B2 | 11/2007 | Sharp et al. | |
| 9,163,308 | B2 * | 10/2015 | Bi | ......................... C23C 16/402 |
| 9,188,524 | B2 * | 11/2015 | Yamasaki | .......... G01N 15/1459 |
| 9,239,405 | B2 * | 1/2016 | Buchanan, III | .......... G01V 8/10 |
| 9,372,072 | B2 * | 6/2016 | Ito | ......................... G01B 11/08 |
| 9,581,494 | B2 * | 2/2017 | Weiβ | ....................... G01J 3/18 |
| 2006/0028727 | A1 * | 2/2006 | Moon | .................. G03H 1/0011 359/569 |

(Continued)

*Primary Examiner* — Sang Nguyen
(74) *Attorney, Agent, or Firm* — C. John Brannon; Brannon Sowers & Cracraft PC

(57) ABSTRACT

A method for monitoring air particulates, including positioning a particulate capture medium, flowing a predetermined volume of air over a particulate capture medium to yield a test sample, measuring the temperature and humidity of the air to generate environmental information, generating optical interrogation data from the test sample, storing the optical interrogation data, and analyzing the optical interrogation data to identify and quantify particulates.

5 Claims, 18 Drawing Sheets

(56) References Cited

U.S. PATENT DOCUMENTS

| | | | |
|---|---|---|---|
| 2007/0063859 A1* | 3/2007 | Twerdochlib | F01D 17/02 340/679 |
| 2008/0192246 A1* | 8/2008 | Neiss | G01J 3/02 356/301 |
| 2008/0229930 A1 | 9/2008 | Jordan et al. | |
| 2008/0246963 A1* | 10/2008 | Nakajima | G01N 15/0205 356/336 |
| 2009/0097020 A1* | 4/2009 | Treado | G01N 21/64 356/301 |
| 2009/0268201 A1* | 10/2009 | Call | G01N 15/0625 356/338 |
| 2010/0261280 A1 | 10/2010 | Black et al. | |
| 2012/0315666 A1 | 12/2012 | Fujioka et al. | |
| 2013/0021607 A1* | 1/2013 | Kanvinde | G01N 21/0332 356/337 |

\* cited by examiner

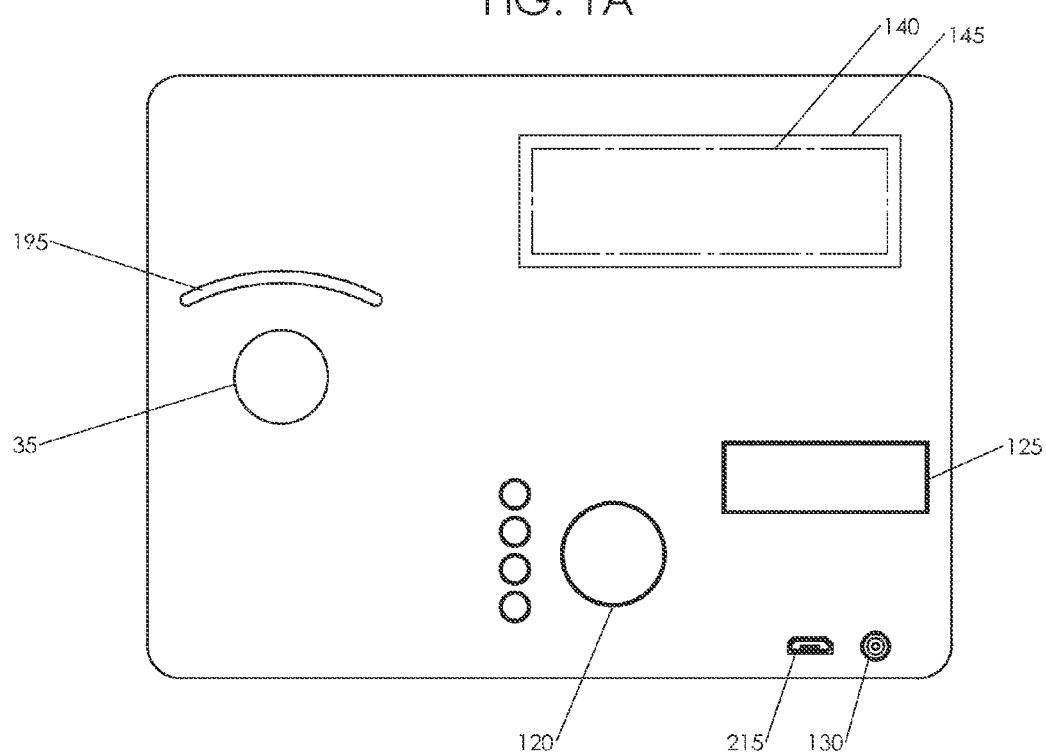

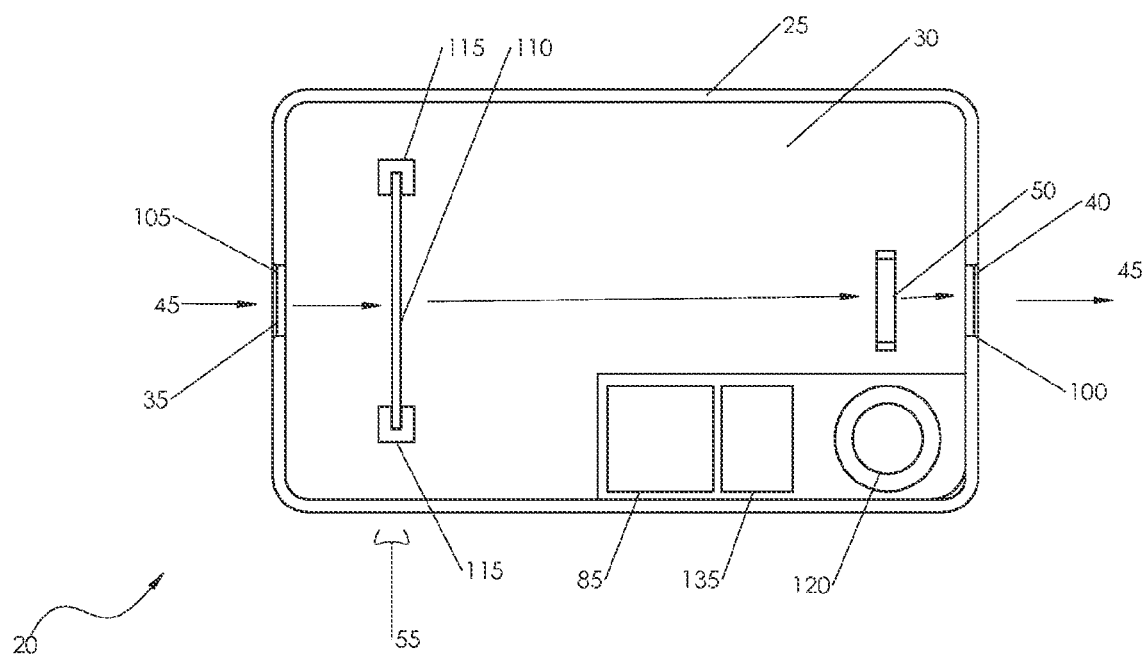

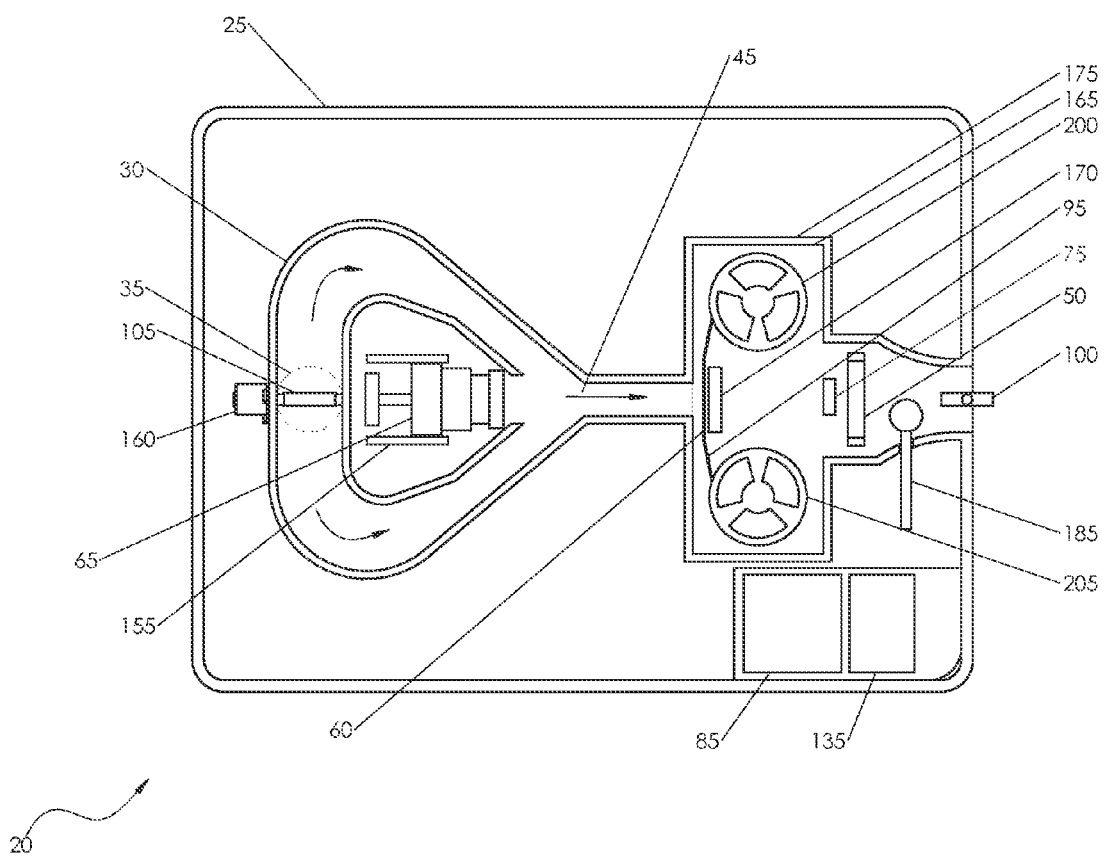

METHOD OF ANALYZING AIR QUALITY

CROSS REFERENCE TO RELATED APPLICATIONS

This utility patent application claims the benefit of, and priority to, U.S. provisional patent application Ser. No. 62/068,643, titled AIR QUALITY ANALYZING APPARATUS AND METHOD OF ANALYZING AIR QUALITY, filed on Oct. 25, 2014.

TECHNICAL FIELD

The present novel technology generally to environmental engineering and, more particularly, to an apparatus for sampling and analyzing air quality and a method of collecting and remotely analyzing air quality, including identifying and quantifying particulates.

BACKGROUND

Much of the Earth's population spends a great deal of time indoors. Modern buildings tend to be far less drafty and are better sealed than their older counterparts, and have sealed air systems providing better control air environments. Similarly, people now spend time in increasing amounts of time in cars, airplanes, ships, underwater chambers, and other spaces with recirculated air. Due to the prevalence of allergies, the increased amount of time that people spend indoors, and an overall increase in awareness of air quality issues, people are more rigorously evaluating the quality of the air and airborne pollutants in enclosed and even open spaces. Indoor air quality is receiving increased attention and evaluation, and many consumers desire evaluation of the air in their environment.

Thus, there is a need for an efficient and inexpensive system and method of providing air quality analysis and, in particular, a system of capturing particulates within air and evaluating the nature and quantity therein. There is also a need for devices to obtain aliquots of air and rapidly capture and convey information about the nature and quantity of particulates therein. The present novel technology addresses these needs.

BRIEF DESCRIPTION OF THE DRAWINGS

The accompanying drawings, which are incorporated into and form a part of the specification, illustrate one or more embodiments of the present novel technology and, together with the description, serve to explain the principles of the novel technology. The drawings are only for the purpose of illustrating embodiments of the novel technology and are not to be construed as limiting the novel technology.

FIG. 1A depicts a top view of an air sampling and quality analysis apparatus according to a first embodiment of the novel technology.

FIG. 2 depicts a cross section view of an air sampling device according to a first embodiment of the novel technology.

FIG. 10 depicts a cross section top view of an embodiment of an air sampling and quality analysis apparatus.

DETAILED DESCRIPTION

Figure 1B:
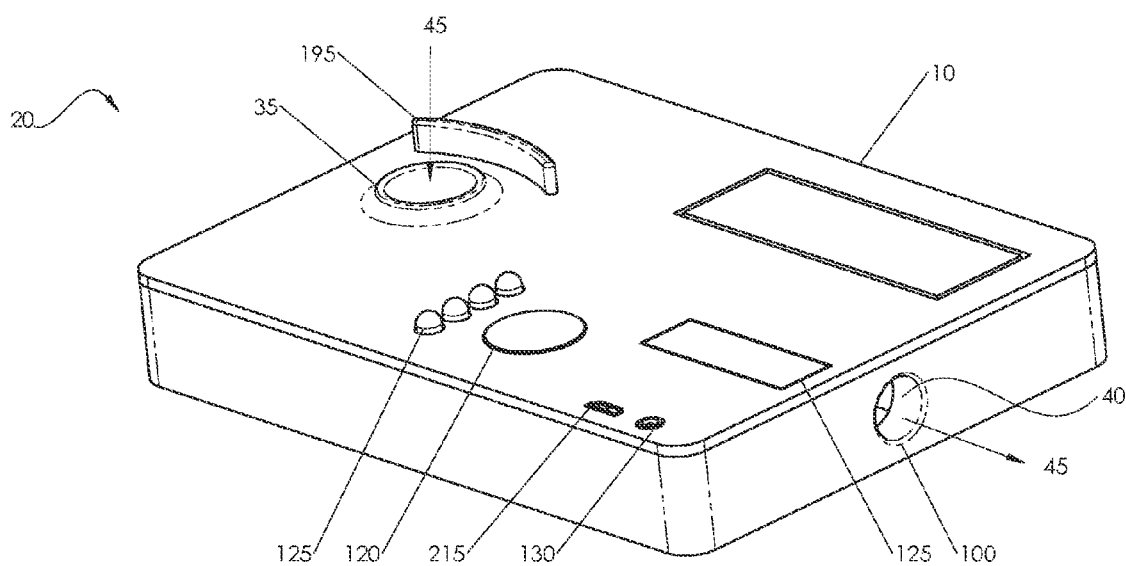
FIG. 1B depicts a perspective view of an air sampling and quality analysis apparatus according a first embodiment of the novel technology.
Figure 3:
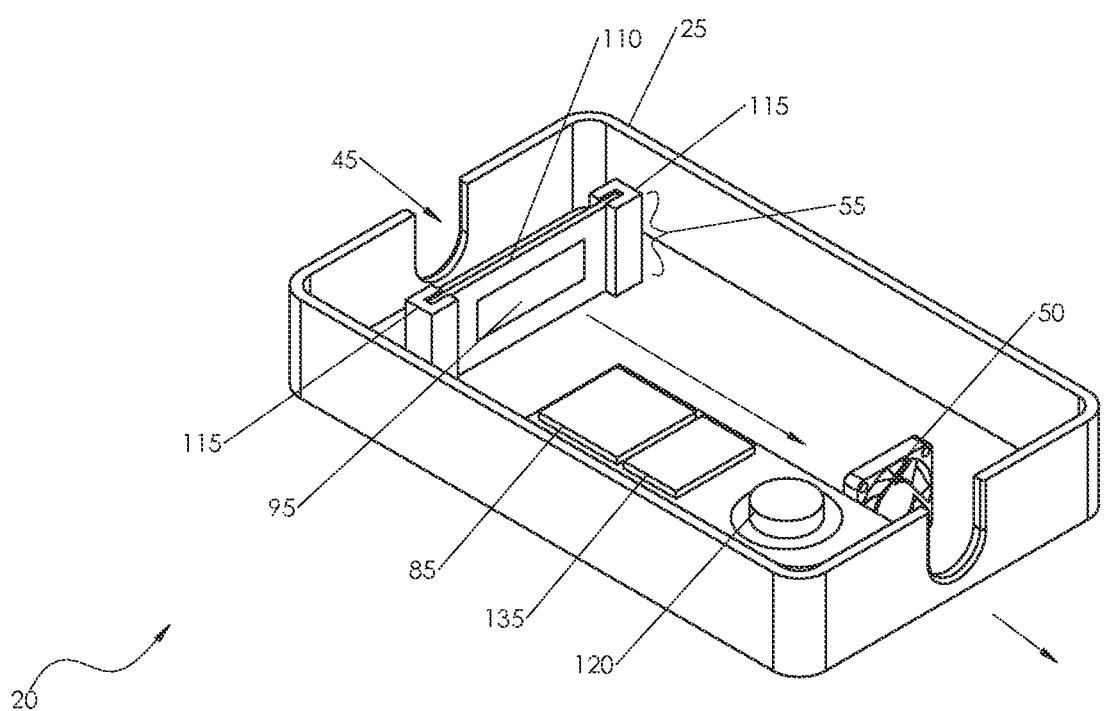
FIG. 3 depicts a perspective view of an air sampling device according to a first embodiment of the novel technology with the top cover removed for clarity in showing the internal components of the first embodiment.
Figure 4:
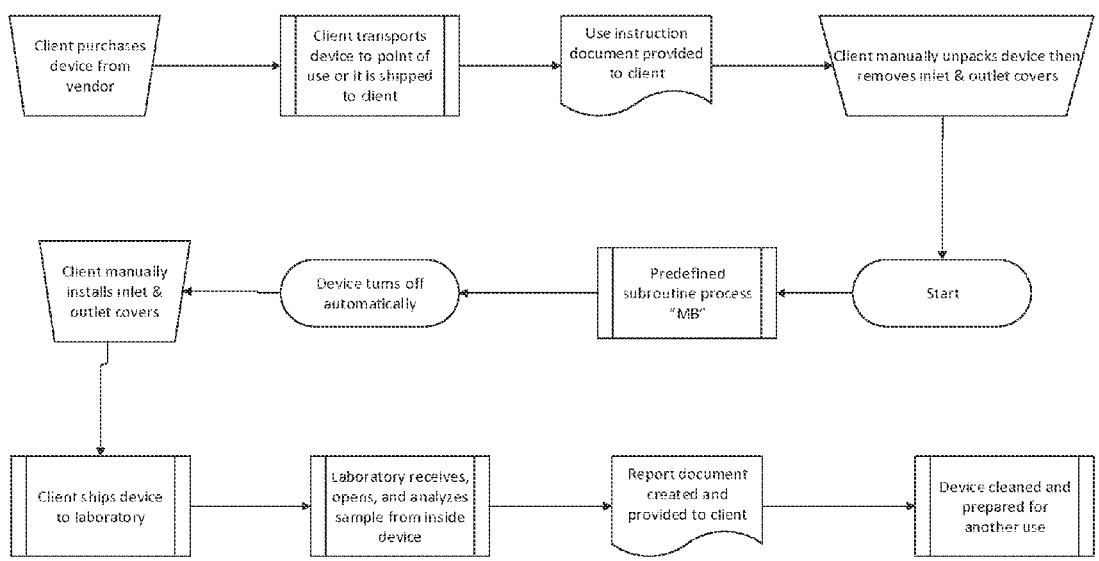
FIG. 4 depicts a flow chart of a method of air sampling and analysis according to one embodiment of the novel technology, which may utilize the first embodiment as shown in FIGS. 1-3.
Figure 5:
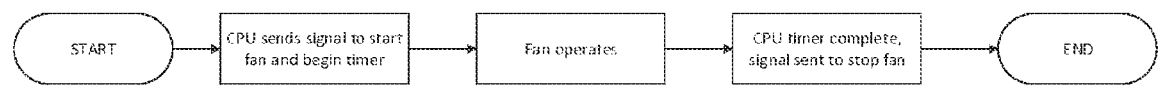
FIG. 5 depicts a flow chart of subroutine MB within the method of air sampling and analysis as provided in FIG. 4.
Figure 6A:
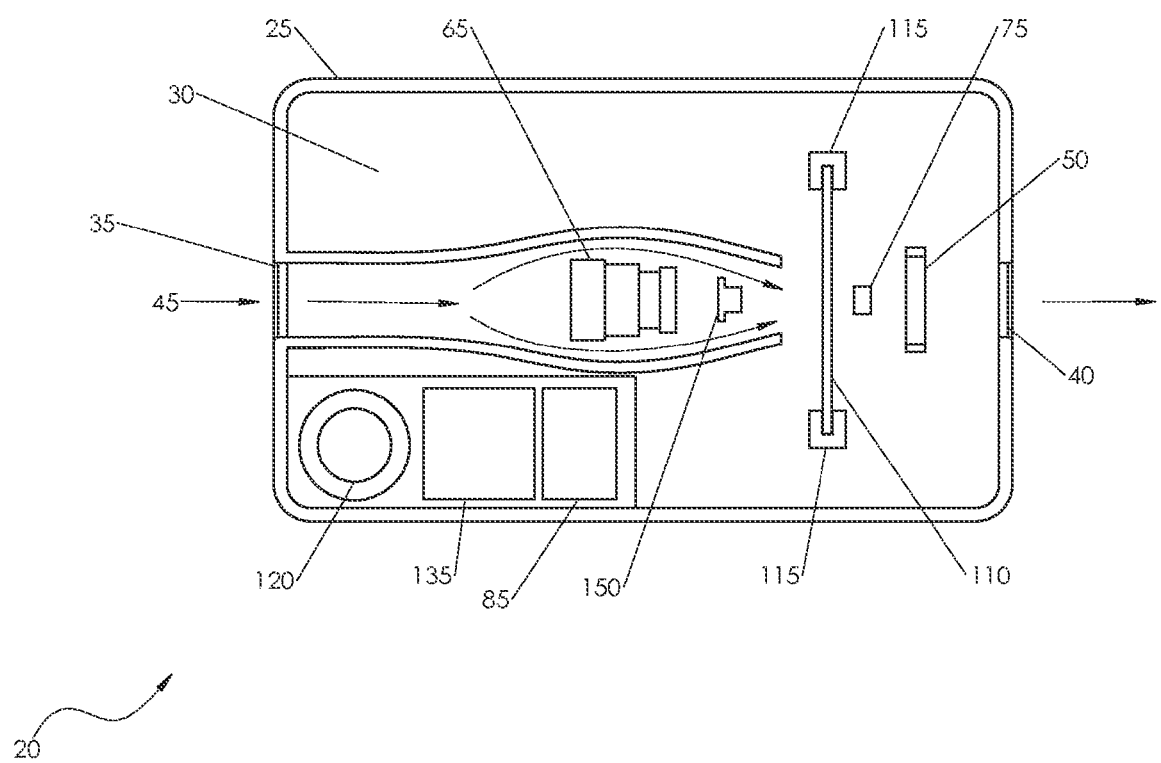
FIG. 6A depicts a cross section top view of an air sampling device and quality analysis apparatus according to a second embodiment of the novel technology, with the top cover removed for clarity in showing the internal components of the second embodiment.
Figure 6B:
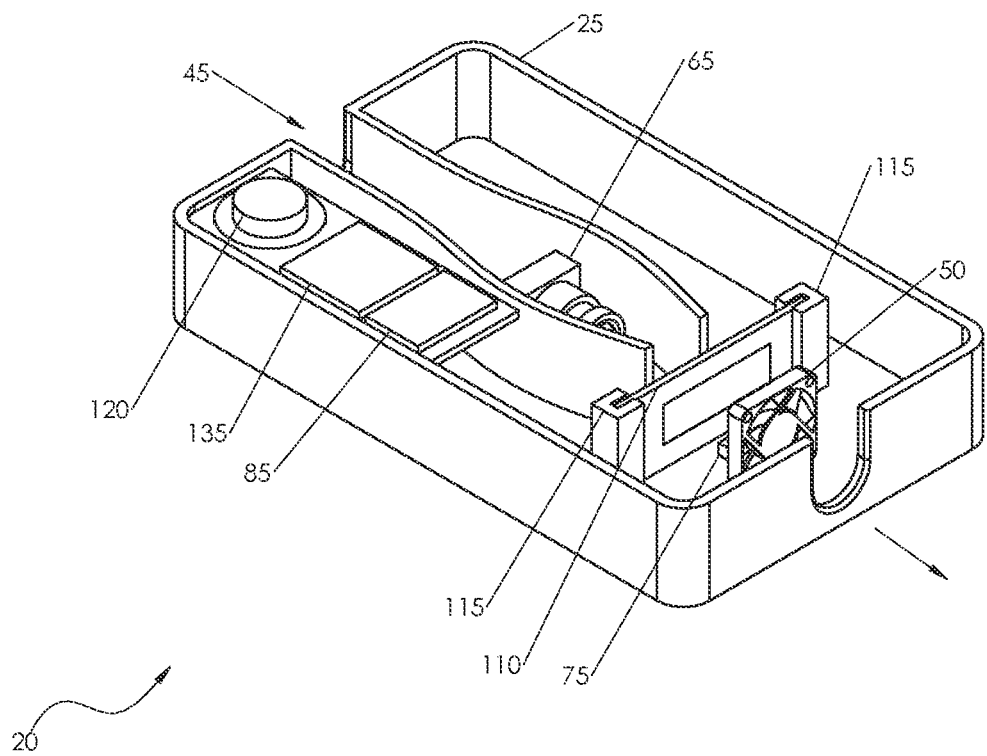
FIG. 6B depicts a perspective view of an air sampling device and quality analysis apparatus according to a second embodiment of the novel technology, with the top cover removed for clarity in showing the internal components of the second embodiment.
Figure 7:
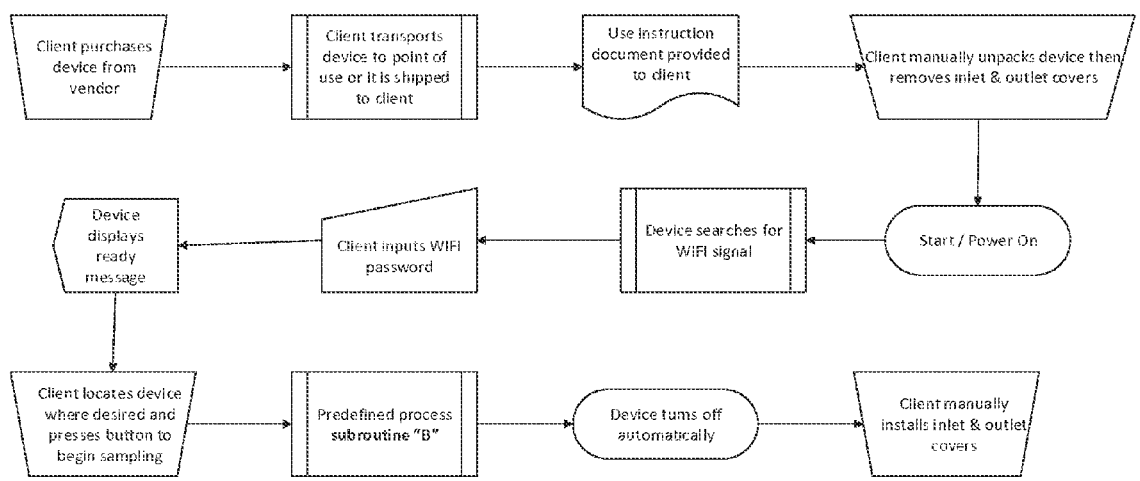
FIG. 7 depicts a flow chart of another method of air sampling and analysis according to another embodiment of the novel technology, which may utilize the device as shown in FIG. 6.
Figure 8:
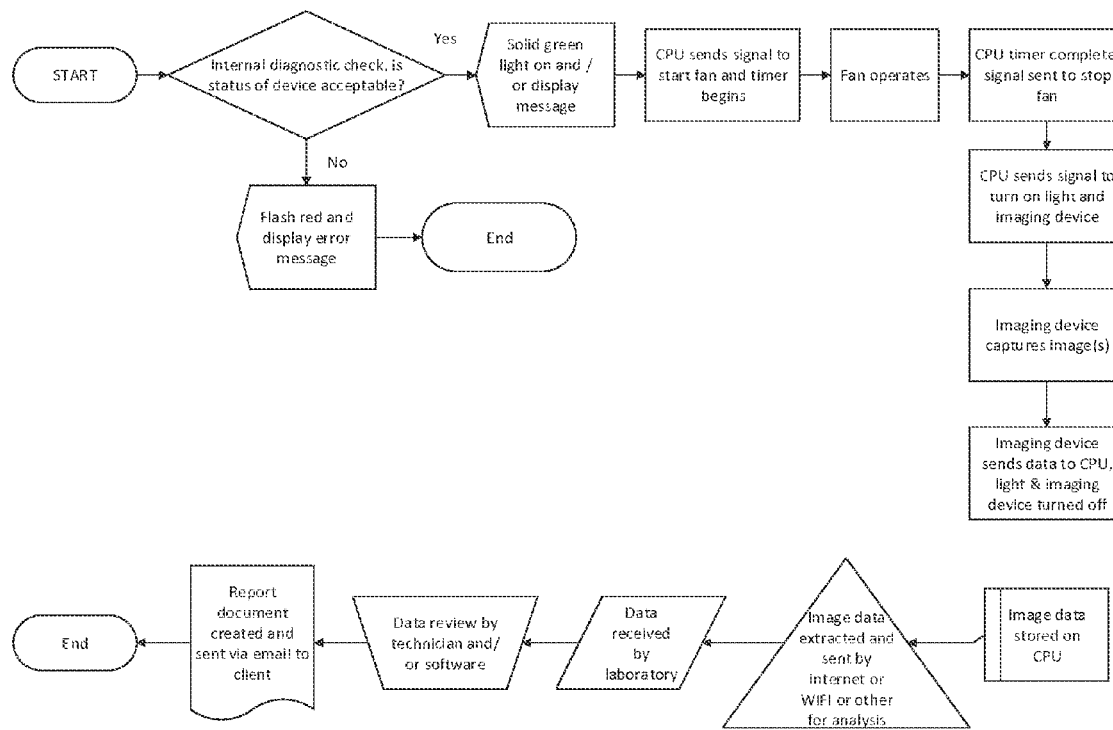
FIG. 8 depicts a flow chart of subroutine B within the method of air sampling and analysis as provided in FIG. 7.
Figure 9A:
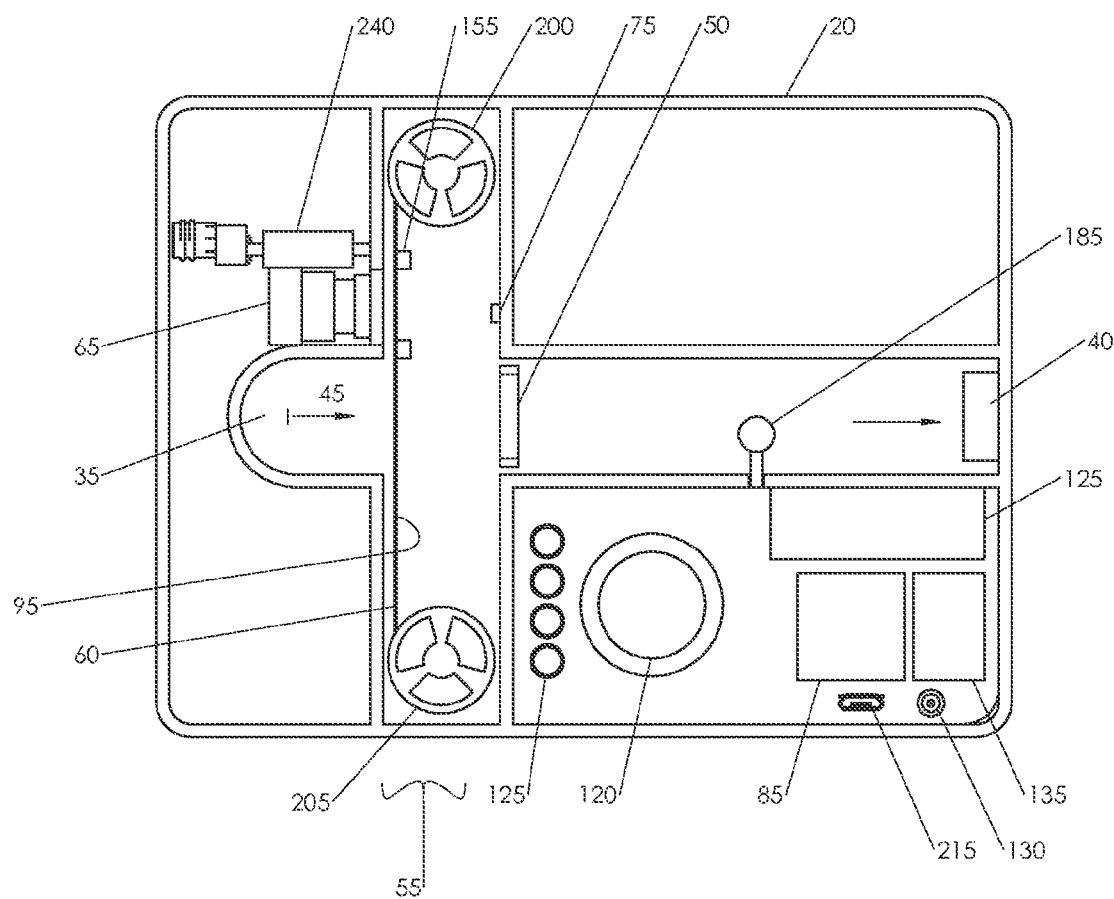
FIG. 9A depicts a cross section front view of an air sampling device and quality analysis apparatus according to a third embodiment of the novel technology with the top cover removed for clarity in showing the internal components of the third embodiment.
Figure 9B:
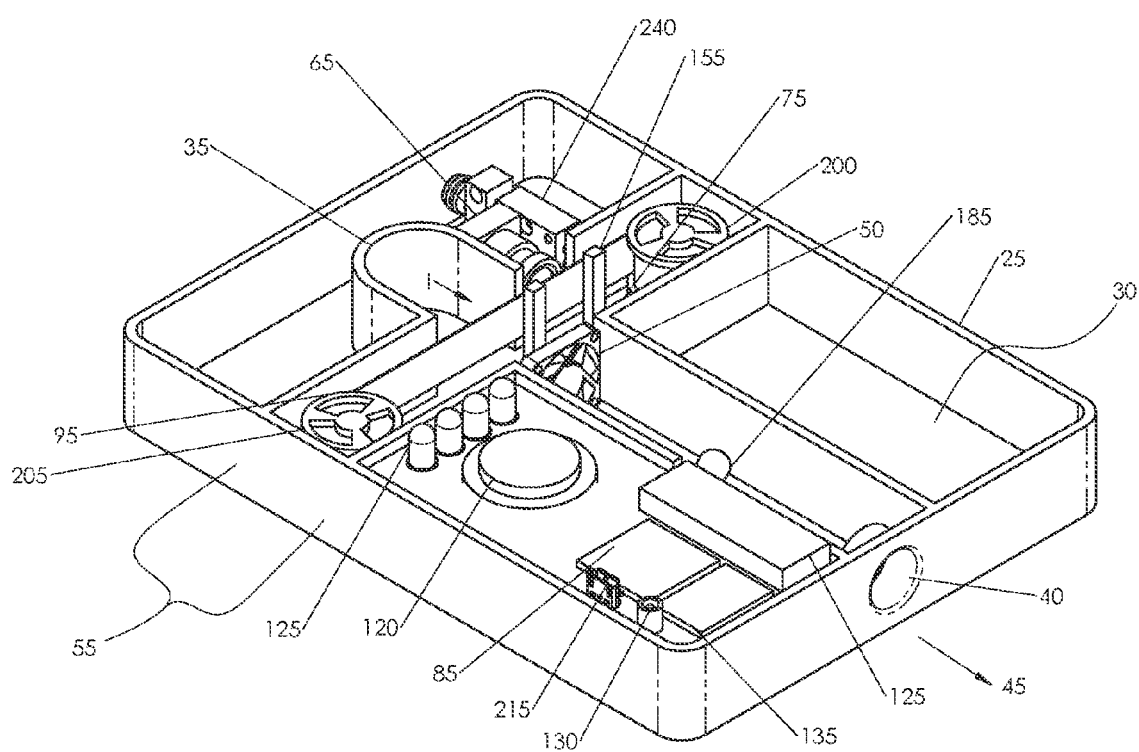
FIG. 9B depicts a perspective view of an air sampling device and quality analysis apparatus according to a third embodiment of the novel technology with the top cover removed for clarity in showing the internal components of the third embodiment.
Figure 11:
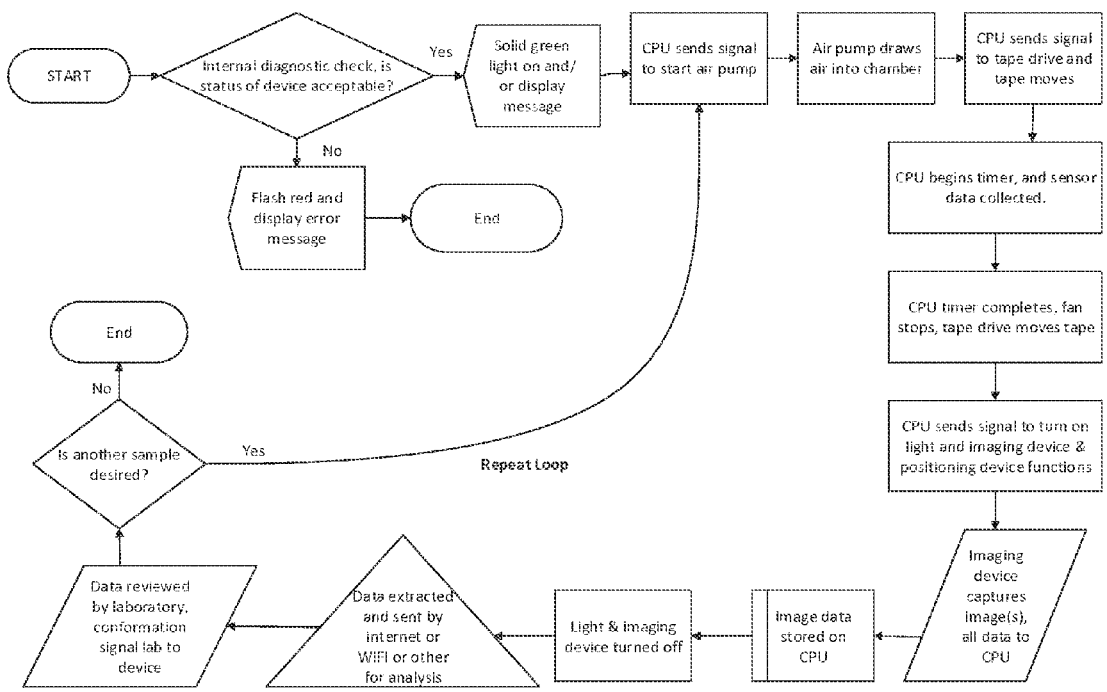
FIG. 11 depicts a flow chart of an embodiment of the method of air sampling and analysis of the novel technology.
Figure 12:
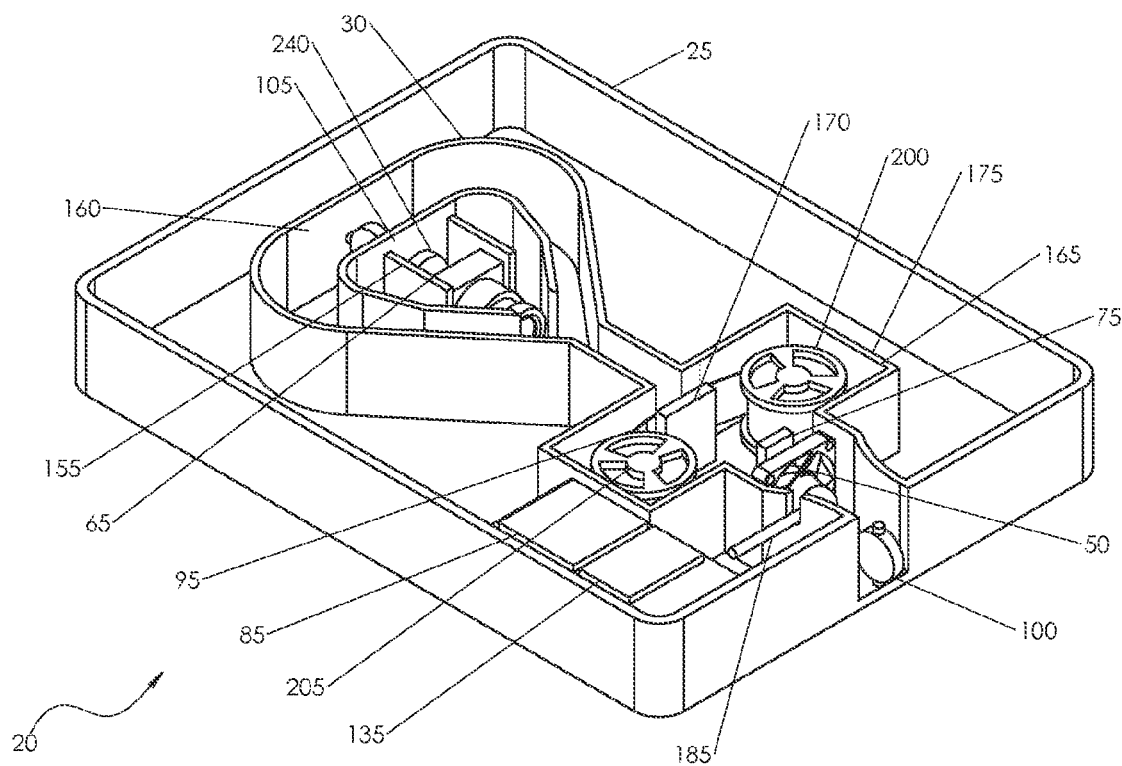
FIG. 12 depicts a cross section front view of an air sampling and quality analysis apparatus according to one embodiment of the novel technology.
Figure 13:
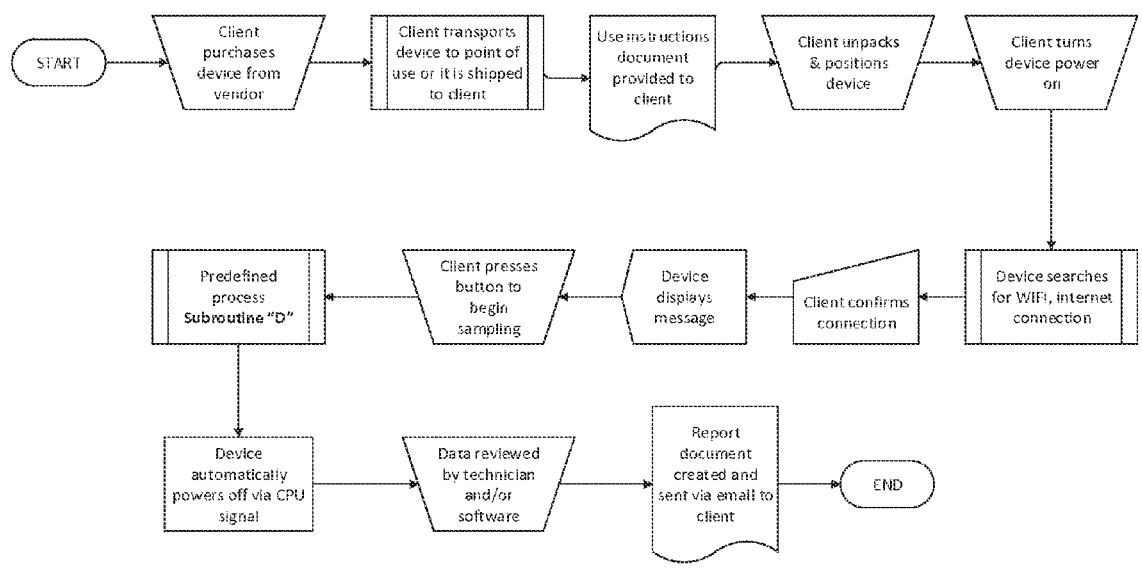
FIG. 13 depicts a flow chart of another method of air sampling and analysis according to another embodiment of the novel technology, which may utilize the device as shown in FIG. 12.
Figure 14:
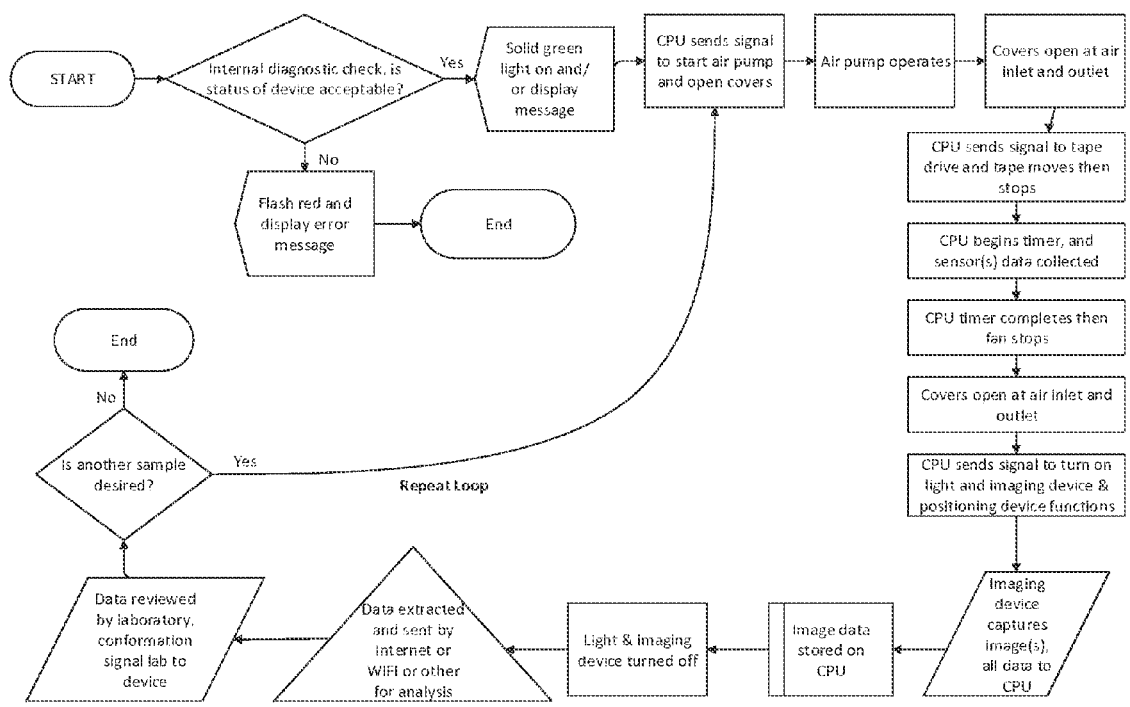
FIG. 14 depicts a flow chart of subroutine D within the method of air sampling and analysis as provided in FIG. 13.

For the purposes of promoting an understanding of the principles of the novel technology and presenting its currently understood best mode of operation, reference will now be made to the embodiments illustrated in the drawings and specific language will be used to describe the same. It will nevertheless be understood that no limitation of the scope of the novel technology is thereby intended, with such alterations and further modifications in the illustrated device and such further applications of the principles of the novel technology as illustrated therein being contemplated as would normally occur to one skilled in the art to which the novel technology relates.

Embodiments of the novel technology relate to a device, system, or method for the analysis of air and/or particulate matter in air. The device may be stationary or portable, and may operate on battery or line power. The system may be placed in virtually any location, including but not limited to a home, hospital, office, vessel, passenger car, vehicle, aircraft, or other enclosed or open spaces. Data and/or images from one or more air samples may be collected by an embodiment of the device according to the novel technology and, in some embodiments, the data and/or images may be transmitted by the device to a remote location using any convenient communication method known in the art, including but not limited to wireless or wired networks, or by physical removal of air samples as described herein, whereupon said samples may be conveyed to a remote site for evaluation and/or analysis by any convenient transport.

FIGS. 1-15 illustrate the present novel technology, a system 20 for analyzing the particulate quality of ambient air. The system 20 typically includes a housing or enclosure 25 defining an interior volume or flow chamber 30, an air inlet port 35 and an air outlet port 40 typically positioned on opposite sides of the housing 25 and defining an air flow pathway 45 therebetween, an air flow actuator device 50 (such as an air pump, fan, or the like) energizable to generate flowing air through the inlet 35, along the air flow pathway 45 through the interior volume 30, and out the exit port 40. A particulate collection device 55 is positioned within the interior volume 30 and in the air flow pathway 45. The particulate collection device 55 typically includes an adhesive surface or sticky side 60 that is typically positioned in the air flow pathway 45 facing the inlet port 35, such that when the pump 50 is energized, air flows onto and over the sticky side 60.

An optical sensor 65, such as a camera, imaging device, or the like, is positioned to optically interrogate the sticky side 60. Typically, the camera 65 has a field of view or focal plane 70 that intersects the particulate collection device 55 and/or the sticky side 60 such that the sticky side 60 may be sharply imaged. The imaging may be passive, such as a digital image generated by a digital camera 65, or active, such as by manipulation of a light beam from an optical sensor system 65 having a laser, LED or like source 75 positioned to shine a beam onto and/or through the sticky side 60 to be reflected/refracted/scattered/transmitted to appropriately positioned light sensors 80. The optical sensor 65 is connected in electric communication with an electronic controller 85, and image/sensor data is transmitted to the electronic controller 85 for analysis and storage. The electronic controller 85 is typically connected in electric communication with a remote memory 90.

According to some embodiments of the novel technology include apparata that comprise an exterior housing 20 and an air pump 50, such as a fan, to draw air into the housing apparatus. Air flows into an inlet opening in the apparatus 20 as a result of lower pressure caused by the air pump 50. Alternately, a fan 50 could be placed at the inlet opening to push air through the device 20 as a result of higher pressure. The air to be sampled enters into one or more ducts or chambers 30 that may contain laminar flow vanes to help define the air flow path 45 or, in other embodiments, the air can generally flow through open space 30 in the interior of the apparatus 20 and then onto and past a particulate impact device 55. The particulate impact device 55 may be comprised of a (typically adhesive) collection member 95, such as a membrane, film, tape, slide, filler or the like to which particulate matter may adhere to be collected. Air exits past the air pump 50 and discharges the apparatus through an exhaust port 40, which in some embodiments may have a cover 100. Likewise, the air inlet port 35 may have a port cover 105.

In embodiments where the particulate impact device 55 is a flat slide or membrane, the particulate impact device 55 may be held in place by one or more slide holders 115 for holding a slide frame 110 supporting and, typically, centering, a strip or portion of film or membrane 95. Such a slide holder 115 may be a separate component, or an integrated piece of the casing or other component.

The exterior housing 25 may have an optional dust brow 195 and/or an optional air inlet movable cover 105. A power actuation switch 120 is typically provided on the exterior of the apparatus in any position practicable, and is connected between the power source 135 and the air flow actuator 50 and/or optical system 65 and/or controller 85. Similarly, an optional display 125 may be present on the exterior of the housing 25 and connected in electric communication with the controller 85. The display 125 may provide control messages to the system 20, may provide device messages and warnings, and/or may provide direct feedback to the consumer to indicate a level of concern regarding indoor environment, such as high humidity, high temperature, high particulate counts, high mold counts, or even after analysis the level of particulate pollutants and/or device status. The exterior housing 25 may optionally include a port 130 for an external power supply. The exterior housing 25 may also optionally include one or more hatches 140 with covers 145 to 40 allow for access to the internal device, such as for replacement of particulate impact devices 55, membranes or filters 95, and like components.

In some embodiments of the present novel technology, the apparatus 20 also includes an image capture device 65. This image capture device may be located anywhere within or without the apparatus housing 25 such that an image of particles on the particulate impact device 55 may be appropriately captured. Thus, the image capture device 65 may be located on the same side of the particulate impact device 55 as the actual particles, captured, or may be between the particulate impact device 55 and the air pump 50, so as to view and digitally record and/or transmit images of the particulate matter captured on the other side 60 of the particulate impact device 55 and in line with the direction of flow of air, or may also be positioned at other angles within or even outside the housing 25. The image capture device 65 does not have to be directed at the sticky side 60 currently in the air flowpath 45, but may instead interrogate images on membranes or films 95 that have been advanced and are no longer in the line of air flow 45 in the device 20. The image capture device 65 may comprise a camera capturing still photographs or images or a video camera for real-time imagery. The optical sensor 65 may also include an integrated microscope or zoom lens assembly 150 and/or imaging capturing methods and/or specialized software to enhance and/or magnify the view of the particulate impact device and particles. The particles may be viewed and illuminated by light sources 75 which may shine from the front, side and/or back of the particulate capture device 55. Control of the focus of the camera 65, microscope 150, or other components of the image capture device 65 may be facilitated by the electronic controller 85, or via remotely controlled movement of the camera and/or microscope 65, 150, or other mechanical positioning guides 155. Within the airstream 45 of the air being sampled may be located one or more sensors 65, 80, 185 to monitor or measure air flow velocity, rate, or other properties.

In this embodiment of the novel technology, microscopic images of particulate matter captured on the membrane/tape/slide/filter are produced. The images can be stored within the device and/or transmitted and stored via communication systems, computer systems, WIFI, or the internet to a remote location for analysis by a person or specialized software systems. The types and quantities of fungal mold spores that are present can be identified as well as the types and quantities of other particulate matter that may be present.

In another embodiment of the device, additional sensors may be connected to, or placed on or within the device to detect, record, store, and transmit additional data such as air temperature, humidity, relative humidity, and due point data at the time of the sample and/or during periods of time prior to or following the time sampling is conducted. With this feature, a record over time of such data can be obtained and analyzed.

In an embodiment of the novel technology, air enters the device 20 through and air inlet port 35 in the exterior housing 25. The air inlet port 35 is equipped with an optional movable air inlet cover 105. From the air inlet port 35 air enters the enclosed air flow chamber 30. An inlet cover actuator 160 may be used to control quantity of air to enter the chamber, and the cover actuator 160 may in turn be operationally connected to and controlled by the electronic controller 85. The flow of air may likewise be controlled the electronic controller 85 adjusting the air pump 50. An air aliquot passes through the enclosed air flow chamber 30 and makes contact with the exposed portion of the particulate impact device 55, which in this embodiment is shown as a membrane tape cassette 165. Particulates in the air contact and adhere to the membrane 95 supported by the membrane tape cassette 165. The membrane tape cassette 165 is held in place by a membrane cassette receptacle 175. Within the receptacle 175, a support table 170 may be present to keep the exposed portion 60 of the membrane 95 in place, and this support table 170 may be adjusted either manually (via screws or other adjustment methods) or via electronic adjustment/actuation instructions provided by the electronic controller 85.

The image capture device 65 is typically an imaging camera with a light source 75. Guides 155 support and secure the imaging camera 65. The focus and positioning of the imaging camera 65 may be controlled by the electronic controller 85. An additional light source 75 provides optional backlighting for effective capture of an image of the particles on the membrane. After making contact with the exposed portion 60 of the membrane 95, wherein particles in the air impact and captured by the membrane 95, the air exits the embodiment device via the exhaust 40, which in FIG. 12 includes a movable exhaust air cover 105, which may be a rotating cover, valve, or the like, but can take the form of any one-way valve. The light source 75, central processing and control module 85, actuators 160, image capture device 65, and other systems that require power are powered by a power supply system 135, which may include a battery or other electrical sources.

An advantage of the membrane tape cassette 165 as a particulate impact device 55 is that a series of air samples may be captured and physically spooled and stored, such that images may be generated as the samples are taken or later, as desired, over a period of time, allowing multiple samples for review and analysis.

Another advantage of the novel technology is the ability of the device 20 to be programmable so it may automatically cycle on and off according to a pre-determined schedule, environmental changes as detected by sensor inputs, or manual inputs. The automatic and programmable control function allows more effective air sampling because the device 20 can be run for many short cycles over extended periods of time thus yielding more representative data, analysis, findings, results, and conclusions in comparison to a single sample that may be significantly affected by anomalous events such as a homeowner using their fireplace, a person painting a room inside the house, or having carpets cleaned inside a residence.

Another advantage of some device embodiments of the novel technology is that it brings together, in one apparatus, the sampling/collection of air samples with the analysis of the same sample. The device 20 may facilitate both the collection and analysis functions. The device 20 can be installed in one location over an extended period of time for multiple samplings, or the device 20 may be delivered to a location for a use in a short period of time. At the sample location a user may own or lease the device 20, or a user may request a service person to deliver, operate, and remove the device.

The rate and quantity of air flow used to gather an air sample may be varied to facilitate predetermined or desired air sample volumes, as well as to confirm proper function of the device 20. In some embodiments, the device 20 may further include a sell-calibrating feature to ensure proper air flow during its operation. The air flow is typically between one liter/minute and fifty liters/minute, more typically about fifteen liters/minute, although other rates may be selected. Cycle time or duration of air flow for an individual test is typically between one minute and thirty minutes, more typically about ten minutes, although shorter or longer cycle times may be selected. It is envisioned that in some applications, cycle time may be on the order of days, weeks, or even longer. For typical cycle time/flow rate combinations, the typical volume of air urged through the inner volume 25 will be about one hundred and fifty liters.

In some embodiments of the device 20, at least one sensor 185 may be located in the air stream to provide electronic feedback to the electronic controller 85 and/or a remote computer or control module 190 which in turn regulates the operation of the air pump/fan. The sensor 185 may be a hot wire type, a temperature sensor, a humidity sensor, a pressure sensor, an anemometer, or other types of sensors and combinations thereof that would provide data useful for analysis. It is envisioned that temperature and humidity data will be collected for each test cycle, and that such data will be archived to provide a history.

In some embodiments of the novel technology, the air pump 50 in the air sampling device 20 may be adjusted to control the flow of air therethrough, either locally via manual adjustment, locally via electronic controller 85 adjustment, or via remote inputs. In the embodiments comprising manual local control of air flow volume per unit of time, the control of air flow may be achieved by a variable potentiometer in series with a power supply 135 for the air pump 50. The potentiometer may be located on a surface of the enclosure 25, or may protrude through a surface of the enclosure 25, such that is able to be adjusted without opening the enclosure 25. In the embodiments which comprise remote control of air flow volume per unit of time, computer executable instructions may be received from a remote user through wireless transceiver 220 where they are communicated to controller 85 for execution, whereby the execution of these instructions causes the air pump 50 to increase or decrease its output, resulting in an increase or decrease of air flow volume per unit of time (see, for example, FIG. 15). In this manner, the air flow volume per unit of time of the sampled air may be adjusted either locally or manually in order to meet air testing requirements.

In some embodiments of the novel technology, the inner workings of air sampling system 20 may be designed to facilitate keeping the system 20 clean and free of foreign material or build-up of dust or other such material in the interior of the apparatus. Embodiments of the novel technology, may feature air-tight and/or dust-resistant sealed enclosure 25 with automatically or manually moveable covers 100, 105, such as the protective cover 105 for air inlet 35 and exhaust cover 100 for the exit port 40, shown on FIG. 12 at the air inlet and discharge points. When the device 20 is not operating to take air samples, the covers 100, 105 are normally closed, sealing the inlet and exhaust openings 35, 40. When the device 20 is operating to take air samples, the covers 100, 105 are automatically opened immediately before the air pump/fan 50 is operated, and the covers 100, 105 are then closed after completion of the sampling. All openings 100, 105 in the device housing 25 are typically sealed dust-tight.

Optimally, the ability for dust or dirt to settle onto or near the air inlet opening 35 is minimized by positioning of a dust brow 195, such as that shown in FIG. 1. The dust brow 195 projects from the surface of the device 20 and extends outwardly therefrom to create a ledge or shell above the air inlet 35 and upon which dust or dirt can settle to preclude the material from settling on, in, or near the air inlet 35. The dust brow 195 prevents or minimizes entry of contaminants into the device 20 when the air inlet 35 is opened for testing or the like. In other embodiments in which the air inlet is not vertical, different methods for controlling build-up of dust or dirt near the air inlet opening 35 may be employed.

In some embodiments of the novel technology, the particulate impact device 55 may include a removable and replaceable membrane cartridge 175. The membrane cartridge 175 typically includes first and second spools 200, 205 that support a continuous ribbon of a tape or film 95, typically having an adhesive side 60 that is faced into the air stream 45 during air sampling. Typically, such film 95 is adhesive and transparent. As the membrane 95 is unwound from the first spool 205, the second spool 200 winds up and collects the used membrane ribbon 95, such as in a traditional audio or VHS cassette tape. In embodiments of the novel technology, the cassette 175 is advanced briefly then stopped for each sampling cycle. This allows a fresh section of membrane ribbon 95 to advance into the sampling zone 45. Use of the membrane cassette 165 allows a new and "clean" section of the membrane 95 to be advanced into the air stream 45 each time a new request for sampling is made. Spooling of the membrane 95 controlled by a motor or actuator that advances the membrane ribbon 95 in a controlled manner via an on-board computer 85, control module, or remote input. The membrane cassette 165 may also be advanced manually.

In some embodiments of the novel technology, the membrane cassette 165 is replaced with different means or methods to place or change the membrane/tape, or with different types of capture devices such as spore traps, individual slides, disposable cassettes or slides, that can be either manually or automatically placed when a sample is needed.

At a remote location, review, analysis, storage, or processing of data and/or images transmitted by or stored in the device can be conducted in either real time or after a period of time. Analyses of such may be conducted by either a person and/or a computer system, either which may also control the device. In particular, optical analysis of the test membrane or film 95 will include a counting of the number of particles of a specific and predetermined type, such as mold spores, captured by a predetermined area of test strip 60. For example, optical searching may be done to identify mold spores in general, or to specifically identify which of over 100,000 varieties of mold spore are present and to provide a relative count for each type identified. An advantage of many embodiments of the novel technology is that neither air samples nor particles (analytes) collected from air samples need to be physically transported from a sampling site to a remote location for analysis. However, other embodiments of the novel technology, provide for methods that include sampling within the apparatus with shipment or transportation of the entire apparatus, or portions thereof, offsite for analysis. Preferred embodiments of the device can eliminate the need for a service person to visit a sampling site to gather samples or conduct analysis. Following use of the device, findings, information, measurements, data, reports, determinations, conclusions and related information about the air sample can be communicated, in ways noted above, from the remote location back to the sample location or other locations, or to any person or computerized system.

In some embodiments, device 20 may feature one or more types of imaging devices 65, detection devices, probes, sensors, and analyzers 80, 150, 185 attached to or placed upon or within the housing 25. The device 20 interrogates the sample and gathers data and/or images which may then by transmitted (manually, by mail, phone, computer systems, internet, wireless (Wi-Fi) connections, data chips, radio frequencies, or via other methods) to a remote location. At the remote location, redundant and/or further analysis of the data/images can be conducted by technical personnel, automated systems, recognition software, and/or other analytical methods.

The device 20 may have many different embodiments with differing arrangements of sensors 185 and instruments capable of determining many types of data or characteristics about a material sample that may be a solid, liquid, or gas. The device 20 can be thought of as a miniature laboratory brought to or placed at a location. The device 20 is able to conduct many various analyses of solids, liquids, and gases depending on the type of instruments connected to, placed upon or held within the device. The device 20 may be operated manually or automatically via computerized modules, software, systems, signals, or links with remote locations. The device 20 conducts analysis of samples, gathers data, and facilitates analysis of data to provide information and support the making of determinations, confirmations, or conclusion about a given sample, its constituents, or analytes that may be present.

The types of information that can be gathered using the device 20 are not limited to temperature, humidity, relative humidity, dew point, particle sizing, particle counts, spore counts, spore concentrations, spore type, and analysis of other particulate matter found in air samples such as asbestos fibers, hairs, allergens, insect parts, rusts, and/or molds. Other uses of the device 20 are not limited to single molecules or atoms, but may also comprise complex aggregates, such as a virus, bacterium, *salmonella, streptococcus, Legionella, E. coli, Giardia, Cryptosporidium, Rickettsia*, spore, mold, yeast, algae, amoebae, dinoflagellate, unicellular organism, pathogen or cell. Virtually any chemical or biological compound, molecule or aggregate could be a target analyte.

The device 20 may have embodiments that are suitable for analysis of human or mammalian health not limited to body temperature, weight, height, blood pressure, breath analysis, urine analysis, blood analyses, skin analysis, bacteria, presence of infectious or viral agents, as well as function or condition of eyesight, vision, hearing, and smell. In such embodiments, the need for a person to visit to a health clinic, hospital, or office is eliminated as is the need for a health care professional to visit an individual's location.

The novel technology has device embodiments that are suitable for industrial or commercial applications not limited to manufacturing or processing facilities for: food, farming, agricultural, mining, chemicals, petroleum, pharmaceuticals, biological products, schools, commercial operations, retail stores, manufacturing facilities, industrial sites, restaurants, lodging establishments, transportation vessels, ports, and other spaces.

Advantages of device embodiments of the novel technology are that it provides an all in one device to both sample and analyze a solid, liquid, or gas. Some embodiments of the novel technology provide data or image transmission to a remote location by various communication or computerized systems.

Utilizing the method and system embodiments of the novel technology that include remote control of the device 20 can eliminate the need for a service person to visit sampling site for various purposes. In some embodiments of the novel technology, a consumer may purchase, rent, or borrow a device 20 for remote capture, and set it up in the space where air is to be analyzed. The entire control of the data capture and analysis may be done remotely using the computerized control features of the capture device 20 in many embodiments of the novel technology.

Though heretofore the novel technology has been described with respect to air sampling, embodiments of the novel technology may be used for other applications as well. For consumers who have an embodiment device, it may be used, for example, to provide a download port for other data, or for sampling of a wide variety of solids, liquids and gases and providing raw data to a remote location for analysis. Additional ports via which data may be downloaded to the controller or directly transmitted to a remote location may optionally be included in some embodiments, such as the port 215.

Embodiments of the device 20 may be further modified as a need arises. Additional or different sensors or devices 150, 185 may be installed based on sampling needs, such as mold, pollens, air particulate, blood work, or analysis of water.

In certain embodiments, the novel technology may incorporate other features such as a smoke alarm, a carbon monoxide alarm, temperature and humidity sensors, a digital microscope, particle counter, and/or volatile organic compound (VOC) meter.

Multiple embodiment devices may be installed in a home or office and feature networking controls/interface, either separately or unified. Embodiment devices may be made compatible with pre-existing software architectures and/or communication protocols.

Embodiments of the novel technology may include security methods for WI-FI use and also for internet access control, such as encryption, password protection, and other known security features (WI-FI is a registered trademark, registration number 2525795, of the Wireless Ethernet Compatibility Alliance, Inc., 3925 W. Braker Lane, Austin Tex.). Embodiments of the novel technology may also include the ability to remotely or locally control the device by manual or automatic methods.

Figure 15:
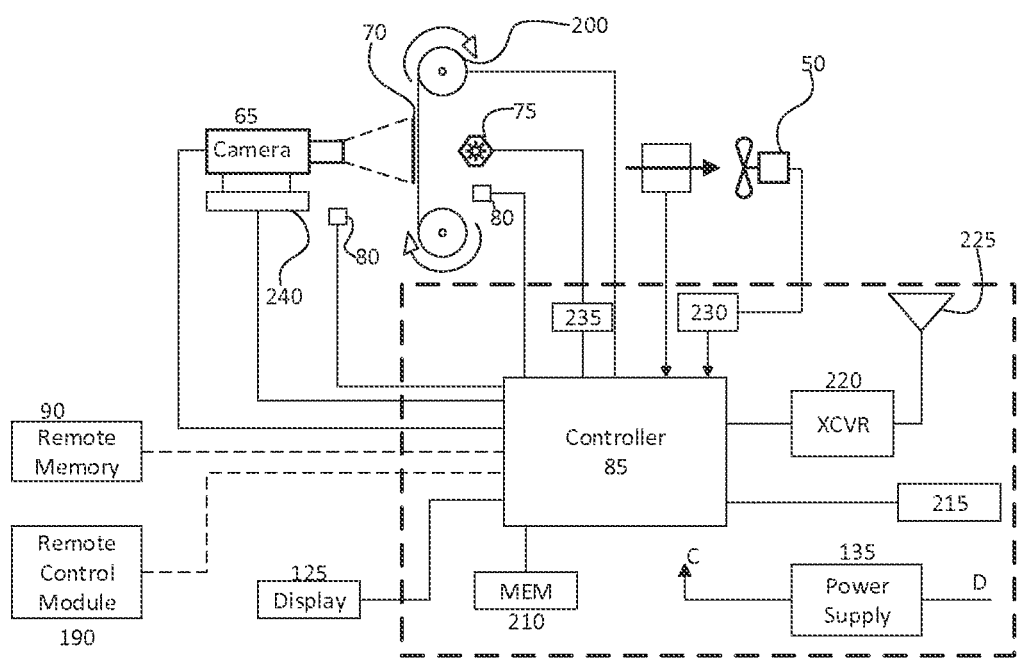
FIG. 15 depicts an electrical block diagram of an embodiment of an air sampling and quality analysis apparatus according to one embodiment of the novel technology.

Referring now to FIG. 15, a block diagram of an embodiment of the novel technology is depicted. The apparatus of the novel technology may comprise a controller 85, which may be any electrical or electronic device capable of executing computer executable instructions, for example a microprocessor, microcontroller, programmable or discrete logic elements, programmable array logic (PAL) circuits, programmable fusible link circuitry, dedicated custom processors, or any other electrical or electronic components capable of executing computer executable instructions. Controller 85 may be in electric communication with non-transitory computer readable medium 210 which may comprise computer executable instructions which may be read and executed by controller 85. Computer readable medium 210 may be, for example, a semiconductor memory, and may comprise any number of semiconductor devices. Controller 85 may be in communication with an external communication port 215 which may be any serial or parallel port for communicating data known in the art, but which may be, for example, a Universal Serial Bus (USB), mirco-USB, Mini-USB, RS-232, RS-485 or any other data port, including a custom data port. External communication port 215 may also be in direct communication with non-transitory computer readable medium 210. External communication port 215 may be utilized to communicate computer executable instructions to controller 85, to load and store computer executable instructions into non-transitory computer readable medium 210, to read information from non-transitory computer readable medium 210 or to otherwise communicate with controller 85 to read system status or to provide control or status monitoring functions using an external computing device.

Still referring to FIG. 15, controller 85 may be in communication with wireless transceiver 220, which may in turn be in communication with antenna 225. Wireless transceiver 220 may be any communications transceiver known in the art such as optical infrared transceiver, fiber optic transceiver or radio frequency (RF) transceiver, and may communicate with external devices by any wireless method, medium or protocol. For example, wireless transceiver 220 may comprise a transceiver operating under the Institute of Electrical and Electronics Engineers (IEEE) 802.11 standard known as Wi-Fi; or, alternatively, may operate under the wireless standard known as BLUETOOTH (BLUETOOTH is a registered trademark, registration number 2909356, of Bluetooth Sig, Inc., Suite 350, 5209 Lake Washington Blvd., Kirkland, Wash. 98033); or may operate at any RF frequency and under any data communication protocol such as 900 MHz, Z-WAVE (Z-WAVE is a registered trademark, registration number 2745803, of Sigma Designs, Inc., 1778 McCarthy Blvd., Milpitas, Calif. 95035), or any other RF frequency and under any protocol, whether standard or custom, analog or digital.

Still referring to FIG. 15, controller 85 may be in communication with air pump drive circuit 230, which in turn may be in communication with air pump 50 which may be any device that is electrically controllable and is able to move an air volume, such as, for example, a fan. Air pump drive circuit 230 may be any circuit that converts a digital output containing air pump drive signals from controller 230 to analog signals suitable for controlling air pump 50. In an embodiment, air pump drive circuit 230 may comprise a digital to analog converter and analog amplifier. In this manner, controller 85 may execute computer executable instructions stored in non-transitory computer readable medium 210 for the purposes of controlling air pump 50 to be in an on state, and off state, and in an embodiment may also control a parameter of air pump 50 directed to controlling airflow volume, such as, for example, fan speed. Likewise, controller 85 may be in communication with drive spool 200 for the purposes of controlling drive spool 200 and therefore to control the movement of particulate impact device 55. In this manner, microprocessor or controller 85 may execute computer executable instructions stored in non-transitory computer readable medium 210 for the purposes of controlling the movement of particulate impact medium 55 by controlling drive spool 200 to rotate, sees rotating, and in an embodiment, control the speed of rotation of drive spool 200. Thus controller 85 controls the movement of air and the movement of particulate impact device 55 so as to have complete control over the collection of air samples.

Controller 85 may be in communication with light source 75, which may be for example an LED light source, and condensing light source or any other light source. Controller 85 may be in communication with light source 75 through light source drive circuit 235. In an embodiment, light source drive circuit 235 may comprise a digital to analog converter and analog amplifier. In this manner, controller 85 may execute computer executable instructions stored in non-transitory computer readable medium 210 for the purposes of light source 75 to be in an on state or an off state. For example, it may be desirable that light source 75 is in an on state to illuminate particulate impact device 55 so that particulate matter collected during the taking of an air sample may be readily visible to camera 65. Camera 65 may be electrical communication with controller 85 such that controller 85 is able to control camera parameters such as on or off, focus, aperture, zoom and other camera parameters. Controller 85 may also be in communication with positioner 240 and is operable to command positioner 240 to be translated so that camera 65 can be brought closer to particulate impact device 55, moved further away from particulate impact device 55, or translated laterally with respect to particulate impact device 55 for purposes of achieving an optimum viewing position of camera 65 relative to particulate impact device 55.

Controller 85 may be connected in communication with display interface 125. Controller 85 may execute computer executable instructions stored in non-transitory computer readable memory 210 causing the display of status information on display 125 as desired by the user.

The electrical and electronic elements of the novel technology may be in communication with power supply 135. Power supply 135 may be in communication with an electrical port designated 130 in FIG. 15 and would may be connected to an external source of supply which may be a DC supply or an AC supply, such as common 115 V AC house current. Power supply 135 may also have an output for connection to the electrical and electronic components of the novel technology, thereby providing power to them. Power supply 135 may also comprise a primary and/or backup battery and backup battery control circuit which operate to provide power to the electrical and electronic components of the system in the event that the external source of power is not present at electrical port 130, or in the event that and external power supply connected at electrical port 130 fails. In this manner, the novel technology is able to operate through power failures or when not connected to an extra source of supply.

While the novel technology has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the novel technology are desired to be protected.

INDUSTRIAL APPLICABILITY

The present novel technology overcomes the shortcomings of the prior art in that it provides an inexpensive system or method of providing air quality analysis and, in particular, a system of capturing particulates within air and evaluating the nature and quantity therein. The system and method of the novel technology is adapted such that embodiments may operate to sample air and to provide either local or remote evaluation of the air quality samples taken by a system of the novel technology.

The present novel technology includes an apparatus and system for the collection of samples and analysis of air and particulate matter in air. The apparatus may be stationary or portable, and may be placed in a variety of locations for a long period of time. The novel technology includes methods of remotely analyzing air quality. The novel technology further includes a method of sampling and analyzing aliquots of air.

What is claimed is:

1. A method for monitoring particulates in air, comprising:
   a. flowing a predetermined volume of air over a particulate capture member to yield a test sample;
   b. by camera, generating optical images of the test sample;
   c. by computer, analyzing the optical images to identify and quantify particulates;
   wherein after b), the particulate capture member is spooled and wound to preserve the test sample and expose a fresh surface for capturing a new sample
   d. after step b and before step c, transmitting the optical images to a remote analyzer;
   e. reporting the particulate content of the air; and
   f. generating an alert message upon detection of predetermined quantities of predetermined particulates by the computer,
   wherein the particulate capture member is a spool of transparent adhesive film.

2. A method for monitoring airborne particulates, comprising:
   a) flowing a predetermined volume of air into a housing and over a first length of particulate capture member disposed therein to yield a first test sample;
   b) by image capture device, generating first optical images of the first test sample;
   c) transmitting the first optical images to a microprocessor memory;
   d) analyzing the first optical images with the microprocessor to identify captured particulates;
   e) analyzing the first optical images to quantify identified particulates;
   f) generating an alert message upon detection of predetermined quantities of predetermined identified particulates;
   g) preserving the first test sample;
   k) after q), flowing a predetermined volume of air into a housing and over a first length of particulate capture member disposed therein to yield a second test sample;
   l) by image capture device, generating second optical images of the second test sample; and
   m) transmitting the second optical images to a microprocessor memory; and
   n) preserving the second sample.

3. The method of claim 2, and further comprising:
   h) concurrently with a) and before d), measuring air temperature and humidity in the housing to yield environmental data;
   i) transmitting the environmental data to the microprocessor memory;
   j) analyzing the optical images and environmental data to yield environment-specific particulate data.

4. The method of claim 2 and further comprising:
   o) after k), generating new images of the first test sample.

5. A method for identifying particulates in the air, comprising:
   a) drawing a predetermined volume of air into a housing defining an airway;
   b) flowing the predetermined volume of air over a first length of adhesive film positioned in the airway to yield a first test sample;
   c) generating a first optical image of the first test sample with a camera;
   d) storing the first optical image in a memory;
   e) analyzing the first optical image with the microprocessor to identify captured particulates;
   f) automatically counting the identified particulates; and
   g) winding the first length of adhesive film onto a spool to preserve the first test sample and to position a second length of adhesive film in the airway to yield a second test sample.

* * * * *